US008461370B2

(12) United States Patent
Uekawa et al.

(10) Patent No.: US 8,461,370 B2
(45) Date of Patent: Jun. 11, 2013

(54) PROCESS FOR PRODUCING 3-(2-CYANO-1-PROPENYL)-2,2-DIMETHYLCYCLOPROPANECARBOXYLIC ACID OR SALT THEREOF

(75) Inventors: Toru Uekawa, Toyonaka (JP); Jun Ohshita, Nishinomiya (JP); Ichiro Komoto, Nishinomiya (JP); Kouji Yoshikawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 78 days.

(21) Appl. No.: 13/255,943

(22) PCT Filed: Apr. 5, 2010

(86) PCT No.: PCT/JP2010/056487
§ 371 (c)(1),
(2), (4) Date: Sep. 12, 2011

(87) PCT Pub. No.: WO2010/117072
PCT Pub. Date: Oct. 14, 2010

(65) Prior Publication Data
US 2012/0016150 A1 Jan. 19, 2012

(30) Foreign Application Priority Data
Apr. 6, 2009 (JP) ................. 2009-091874

(51) Int. Cl.
*C07C 255/31* (2006.01)
*C07C 255/39* (2006.01)
(52) U.S. Cl.
USPC .......................................... 558/407; 560/124

(58) Field of Classification Search
USPC ........................................ 558/407; 560/124
See application file for complete search history.

(56) References Cited

U.S. PATENT DOCUMENTS

| 4,235,805 A | 11/1980 | Lenselink |
| 4,262,117 A | 4/1981 | Brown |
| 4,336,204 A | 6/1982 | Lenselink |
| 4,456,561 A | 6/1984 | Lenselink |
| 5,011,970 A | 4/1991 | Lenselink |
| 6,908,945 B2 | 6/2005 | Mori |
| 2003/0195119 A1 | 10/2003 | Mori |
| 2010/0035985 A1 | 2/2010 | Mori |

FOREIGN PATENT DOCUMENTS

| JP | 54-130540 A | 10/1979 |
| JP | 55-033496 A | 3/1980 |
| JP | 2004-002363 A | 1/2004 |
| JP | 2006-089427 A | 4/2006 |
| JP | 2008-239597 A | 10/2008 |

OTHER PUBLICATIONS

Int'l Search Report issued May 11, 2010 in Int'l Application No. PCT/JP2010/056487.
Int'l Preliminary Report on Patentability issued Nov. 15, 2011 in Int'l Application No. PCT/JP2010/056487.
Ueda et al., "Studies on Chrysanthemic Acid: Part XX. Synthesis of Four Geometrical Isomers of (±)-Pyrethric Acid," Agricultural and Biological Chemistry, vol. 34., No. 7, pp. 1119-1125 (1970).

*Primary Examiner* — Shawquia Young
(74) *Attorney, Agent, or Firm* — Panitch Schwarze Belisario & Nadel LLP

(57) ABSTRACT

A process for producing comprising reacting a 3-formyl-2,2-dimethylcyclopropanecarboxylate and propionitrile in the presence of a base to obtain 3-(2-cyano-1-propenyl)-2,2-dimethylcyclopropanecarboxylic acid or its salt.

10 Claims, No Drawings

PROCESS FOR PRODUCING 3-(2-CYANO-1-PROPENYL)-2,2-DIMETHYLCYCLOPROPANECARBOXYLIC ACID OR SALT THEREOF

CROSS-REFERENCE TO RELATED APPLICATION

This application is a Section 371 of International Application No. PCT/JP2010/056487, filed Apr. 5, 2010, which was published in the Japanese language on Oct. 14, 2010, under International Publication No. WO 2010/117072 A1, and the disclosure of which is incorporated herein by reference.

TECHNICAL FIELD

The present invention relates to a process for producing 3-(2-cyano-1-propenyl)-2,2-dimethylcyclopropanecarboxylic acid or its salt.

BACKGROUND ART 3-(2-cyano-1-propenyl)-2,2-dimethylcyclopropanecarboxylic acid or its salt can be obtained by hydrolysis of the correspondent ester. As a process for producing such a 3-(2-cyano-1-propenyl)-2,2-dimethylcyclopropanecarboxylate, for example, a reaction of a 4-methoxymethyl-2,3,5,6-tetrafluorobenzyl-3-formyl-2,2-dimethylcyclopropanecarboxylate and 2,2-diethylcyclo(1-cyanoethyl)phosphonate (so-called Horner-Wadsworth-Emmons reaction) is known (for example, JP-A No. 2004-2363).

DISCLOSURE OF THE INVENTION

The present invention relates to a novel production method of 3-(2-cyano-1-propenyl)-2,2-dimethylcyclopropanecarboxylic acid or its salt.

That is, the present application relates to the following invention.

[1] A process for producing 3-(2-cyano-1-propenyl)-2,2-dimethylcyclopropanecarboxylic acid or its salt comprising reacting a 3-formyl-2,2-dimethylcyclopropanecarboxylate and propionitrile in the presence of a base.

[2] The process according to [1], wherein the base is a strong base.

[3] The process according to [1], wherein the base is at least one base selected from the group consisting of alkali metal hydroxides, alkaline earth metal hydroxides, transition metal hydroxides, tetraalkylammonium hydroxides, alkali metal alkoxides and phosphazene compounds.

[4] The process according to [1], wherein the base is at least one base selected from the group consisting of alkali metal hydroxides, alkaline earth metal hydroxides, transition metal hydroxides and tetraalkylammonium hydroxides.

[5] The process according to [1], wherein the base is an alkali metal hydroxide or alkaline earth metal hydroxide.

[6] The process according to [1], wherein the base is potassium hydroxide or cesium hydroxide.

[7] The process according to any one of [1] to [6], wherein a 3-formyl-2,2-dimethylcyclopropanecarboxylate and propionitrile are reacted in the presence of a solvent.

[8] The process according to [7], wherein the solvent is an ether solvent or sulfoxide solvent.

[9] The process according to [7], wherein the solvent is tetrahydrofuran or dimethyl sulfoxide.

[10] A process for producing a 3-(2-cyano-1-propenyl)-2,2-dimethylcyclopropanecarboxylate represented by formula (4):

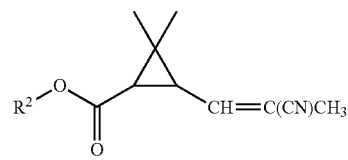

(4)

wherein, $R^2$ represents a chain hydrocarbon group having 1 to 10 carbon atoms or cyclic hydrocarbon group having 3 to 10 carbon atoms each of which optionally have at least one substituent selected from the following Group A;

Group A: halogen atoms, acyl groups having 2 to 7 carbon atoms, alkoxy groups having 1 to 7 carbon atoms optionally having a substituent, alkylthio groups having 1 to 3 carbon atoms and aryl groups having 6 to 10 carbon atoms optionally having a substituent;

comprising a first step of reacting a 3-formyl-2,2-dimethylcyclopropanecarboxylate and propionitrile in the presence of a base, and a second step of reacting 3-(2-cyano-1-propenyl)-2,2-dimethylcyclopropanecarboxylic acid or its salt obtained in the above-described first step and a monohydroxy compound represented by formula (2):

$$R^2\text{—OH} \quad (2)$$

wherein, $R^2$ represents the same meaning as described above; in the presence of a zirconium compound.

MODES FOR CARRYING OUT THE INVENTION

The present invention will be illustrated in detail below.

In the present specification, the 3-formyl-2,2-dimethylcyclopropanecarboxylate (hereinafter, this compound is referred to as "ester compound") is composed of a cyclopropane ring having a formyl group at 3-position, two methyl groups at 2-position and a substituent having an ester bond (COO—) at 1-position.

The ester compound can be obtained by known methods, for example, described in JP-A No. 2006-89427 and the like.

In the ester compound, the group having an ester bond and the formyl group on its cyclopropane ring may be present on mutually the same side of the cyclopropane plane (cis form), or may be present on mutually the opposite sides thereof (trans form), and the trans form is preferable. In the ester compound, the absolute configuration is preferably a (1R,3R) form.

The ester compound includes, for example, compounds represented by the formula I:

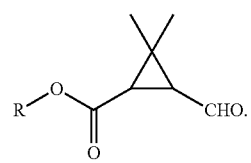

I

In the formula I, R represents an optionally substituted hydrocarbon group. R represents, in general, a chain hydrocarbon group having 1 to 10 carbon atoms or cyclic hydrocarbon group having 3 to 10 carbon atoms each of which optionally be substituted by at least one group selected from the following Group A.

Group A: halogen atoms, acyl groups having 2 to 7 carbon atoms, optionally substituted alkoxy groups having 1 to 7 carbon atoms, optionally substituted alkylthio groups having 1 to 3 carbon atoms and optionally substituted aryl groups having 6 to 10 carbon atoms.

The above-described halogen atom includes fluorine, chlorine, bromine, iodine and the like.

The above-described acyl group having 2 to 7 carbon atoms includes an acetyl group, propionyl group, butyryl group and the like.

The above-described optionally substituted alkoxy group having 1 to 7 carbon atoms includes alkoxy groups having 1 to 7 carbon atoms, such as a methoxy group, ethoxy group and the like; alkoxy groups having 1 to 7 carbon atoms substituted by an alkoxy group, such as a methoxymethoxy group, ethoxymethoxy group and the like; alkoxy groups having 1 to 7 carbon atoms substituted by a benzyl group, such as a benzyloxy group and the like; etc.

The above-described optionally substituted alkylthio group having 1 to 3 carbon atoms includes a methylthio group, ethylthio group and the like.

The above-described optionally substituted aryl group having 6 to 10 carbon atoms includes a phenyl group; a naphthyl group; halogen-substituted phenyl groups, such as a 4-bromophenyl group, 2,3-difluorophenyl group, 2,3,5-trifluorobenzyl group and the like; phenyl groups substituted by an alkoxy group having 1 to 5 carbon atoms, such as a 4-methoxyphenyl group and the like; nitro-substituted phenyl groups, such as a 2-nitrophenyl group, 4-nitrophenyl group and the like; optionally substituted anthranyl groups, such as a 2-(9,10-dioxo)anthranyl group and the like.

The chain hydrocarbon group having 1 to 10 carbon atoms includes alkyl groups having 1 to 10 carbon atoms, such as a methyl group, ethyl group, propyl group, isopropyl group and the like; alkenyl groups having 3 to 10 carbon atoms, such as an allyl group and the like; alkynyl groups having 3 to 10 carbon atoms, such as a propargyl group and the like.

The chain hydrocarbon group having 1 to 10 carbon atoms substituted by a halogen atom includes a 2-chloroethyl group, 2,2,2-trichloroethyl group and the like.

The above-described chain hydrocarbon group having 1 to 10 carbon atoms substituted by an acyl group includes a phenacyl group, p-bromophenacyl group and the like.

The above-described chain hydrocarbon group having 1 to 10 carbon atoms substituted by an alkoxy group includes a methoxymethyl group, methoxymethoxymethyl group, benzyloxymethyl group and the like.

The above-described chain hydrocarbon group having 1 to 10 carbon atoms substituted by an alkylthio group includes a methylthiomethyl group, 2-methylthioethyl group and the like.

The above-described chain hydrocarbon group having 1 to 10 carbon atoms substituted by an aryl group includes a benzyl group, phenethyl group, 4-bromobenzyl group, 4-methoxybenzyl group, 2,3-difluorobenzyl group, 2,3,5-trifluorobenzyl group, 2,3,5,6-tetrafluoro-4-methoxymethylbenzyl group, 2-nitrobenzyl group, 4-nitrobenzyl group, bis(o-nitrophenyl)methyl group, 9,10-dioxo-2-anthranylmethyl group and the like.

The cyclic hydrocarbon group having 3 to 10 carbon atoms includes cycloalkyl groups having 3 to 10 carbon atoms, such as a cyclopropyl group, cyclopentyl group, cyclohexyl group and the like, and aryl groups having 6 to 10 carbon atoms, such as a phenyl group, naphthyl group and the like.

The above-described R is preferably a chain hydrocarbon group having 1 to 10 carbon atoms, more preferably a chain hydrocarbon group having 1 to 4 carbon atoms, further preferably an alkyl group having 1 to 4 carbon atoms.

Examples of the above-described ester compound include 3-formyl-2,2-dimethylcyclopropanecarboxylic acid (C1 to C10 alkyl) esters; 3-formyl-2,2-dimethylcyclopropanecarboxylic acid (C1 to C10 haloalkyl) esters; 3-formyl-2,2-dimethylcyclopropanecarboxylic acid (C2 to C10 alkoxyalkyl) esters; 3-formyl-2,2-dimethylcyclopropanecarboxylic acid (C3 to C10 alkyl) esters; 3-formyl-2,2-dimethylcyclopropanecarboxylic acid (C6 to C10 aryl) esters; and the like.

Specific examples of the above-described ester compound include 3-formyl-2,2-dimethylcyclopropanecarboxylic acid (C1 to C4 alkyl) esters, such as methyl 3-formyl-2,2-dimethylcyclopropanecarboxylate, ethyl 3-formyl-2,2-dimethylcyclopropanecarboxylate, propyl 3-formyl-2,2-dimethylcyclopropanecarboxylate, butyl 3-formyl-2,2-dimethylcyclopropanecarboxylate and the like; 3-formyl-2,2-dimethylcyclopropanecarboxylic acid (C1 to C10 haloalkyl) esters, such as fluoromethyl 3-formyl-2,2-dimethylcyclopropanecarboxylate, fluoroethyl 3-formyl-2,2-dimethylcyclopropanecarboxylate, fluoropropyl 3-formyl-2,2-dimethylcyclopropanecarboxylate, fluorobutyl 3-formyl-2,2-dimethylcyclopropanecarboxylate and the like; 3-formyl-2,2-dimethylcyclopropanecarboxylic acid (C2 to C10 alkoxyalkyl) esters, such as methoxymethyl 3-formyl-2,2-dimethylcyclopropanecarboxylate, methoxyethyl 3-formyl-2,2-dimethylcyclopropanecarboxylate, methoxypropyl 3-formyl-2,2-dimethylcyclopropanecarboxylate, methoxybutyl 3-formyl-2,2-dimethylcyclopropanecarboxylate and the like; 3-formyl-2,2-dimethylcyclopropanecarboxylic acid (C6 to C10 aryl) esters, such as phenyl 3-formyl-2,2-dimethylcyclopropanecarboxylate and the like; etc.

In the present specification, C1 to C10, C2 to C10, C3 to C10, C1 to C4 and C6 to C10 represent the number of carbon atoms of 1 to 10, the number of carbon atoms of 2 to 10, the number of carbon atoms of 3 to 10, the number of carbon atoms of 1 to 4 and the number of carbon atoms of 6 to 10, respectively.

As propionitrile, those commercially available can be used. The use amount of propionitrile is usually 0.8 mol or more with respect to 1 mol of the ester compound. Though propionitrile may be used in excess amount also as a solvent simultaneously, it is used in an amount in the range of preferably 0.8 to 30 mol, more preferably 1 to 3 mol with respect to 1 mol of the ester compound.

The base is an inorganic base or an organic base.

The above-described base is preferably a strong base.

In the present invention, the base is more preferably at least one base selected from the group consisting of alkali metal hydroxides, alkaline earth metal hydroxides, transition metal hydroxides, tetraalkylammonium hydroxides, alkali metal alkoxides and phosphazene compounds.

Examples of the alkali metal hydroxide include lithium hydroxide, sodium hydroxide, potassium hydroxide, rubidium hydroxide, cesium hydroxide and the like.

Examples of the alkaline earth metal hydroxide include magnesium hydroxide, calcium hydroxide, barium hydroxide and the like.

Examples of the transition metal hydroxide include iron (III) hydroxide, chromium(III) hydroxide, nickel(II) hydroxide, copper(II) hydroxide and the like.

Examples of the tetraalkylammonium hydroxide include tetraalkylammonium hydroxides that the number of carbon atoms of an alkyl portion is 1 to 4, such as tetramethylammonium hydroxide, tetraethylammonium hydroxide and the like.

Examples of the alkali metal alkoxide include alkali metal alkoxides that the number of carbon atoms of an alkoxy portion is 1 to 4, such as sodium methoxide, potassium methoxide, sodium ethoxide; potassium ethoxide, sodium tert-butoxide, potassium tert-butoxide and the like.

Examples of the phosphazene compound include 1,1,1,3,3,3-hexakis(dimethylamino)diphosphazenium fluoride, hexakis(1H,1H,3H-perfluoropropoxy)phosphazene, 1-tert-butyl-4,4,4-tris(dimethylamino)-2,2-bis[tris(dimethyl amino)-phosphoranylideneamino]-2Λ,4Λ-catenadi(phosphazene) and the like.

Such a base is more preferably at least one base selected from the group consisting of alkali metal hydroxides, alkaline earth metal hydroxides, transition metal hydroxides and tetraalkylammonium hydroxides; further preferably an alkali metal hydroxide or alkaline earth metal hydroxide; particularly preferably an alkali metal hydroxide. Of them, potassium, hydroxide or cesium hydroxide is particularly preferable.

As these bases, those commercially available can be used. The use amount of the base is in the range of usually 1 to 3 mol, preferably 1.5 to 2.5 mol with respect to 1 mol of the ester compound.

The reaction in the present invention is usually carried out in the presence of a solvent. Such a solvent is not particularly limited providing it is a solvent showing solubility for the base to be used, and it may be an aprotic solvent or may be a protic solvent. Examples of the aprotic solvent include aromatic hydrocarbon solvents, such as benzene, toluene, xylene and the like; aliphatic hydrocarbon solvents, such as hexane, heptane and the like; ether solvents, such as diethyl ether, tert-butyl methyl ether, cyclopentyl methyl ether, tetrahydrofuran, 1,4-dioxane and the like; halogenated hydrocarbon solvents, such as dichloromethane, 1,2-dichloroethane, chlorobenzene and the like; nitro solvents, such as nitrobenzene and the like; amide solvents, such as dimethylformamide, dimethylacetamide and the like; sulfoxide solvents, such as dimethyl sulfoxide and the like; etc. Examples of the protic solvent include alcohol solvents, such as methanol, ethanol, propanol, isopropanol and the like, water, etc. These solvents may be used singly or in combination of two or more. The cyclic ether solvent is preferably a cyclic ether having 4 to 8 carbon atoms. The alkyl sulfoxide solvent preferably has an alkyl group having 1 to 4 carbon atoms.

The above-described solvent is preferably an aprotic solvent, more preferably an ether solvent or sulfoxide solvent, further preferably a cyclic ether solvent or alkyl sulfoxide solvent, particularly preferably tetrahydrofuran or dimethyl sulfoxide. Of them, dimethyl sulfoxide is particularly preferable. The use amount of the solvent is usually in the range of 0.5 to 20 parts by weight with respect to 1 part by weight of the ester compound.

The reaction in the present invention is carried out by mixing an ester compound, propionitrile and a base, if necessary in the presence of a solvent, and the mixing order thereof is not particularly restricted.

The reaction temperature is in the range of usually −20 to 150° C., preferably −5 to 100° C.

The reaction time is in the range of usually 5 minutes to 72 hours. The progress of the reaction can be confirmed by usual means such as gas chromatography, high performance liquid chromatography and the like.

The reaction mixture after completion of the reaction contains 3-(2-cyano-1-propenyl)-2,2-dimethylcyclopropanecarboxylic acid or its salt. The resultant 3-(2-cyano-1-propenyl)-2,2-dimethylcyclopropanecarboxylic acid usually forms a salt with the base used. When such a salt is neutralized, the carboxylic acid is obtained.

The salt 3-(2-cyano-1-propenyl)-2,2-dimethylcyclopropanecarboxylic acid includes salts such as alkali metal salts, alkaline earth metal salts, tetraalkylammonium salts, phosphazenium salts and the like corresponding to the base used. A usual post treatment such as neutralization, water-washing, extraction, concentration and the like can be performed on such a reaction mixture, to isolate 3-(2-cyano-1-propenyl)-2,2-dimethylcyclopropanecarboxylic acid or its salt.

The isolated 3-(2-cyano-1-propenyl)-2,2-dimethylcyclopropanecarboxylic acid or its salt may also be further purified by a usual purification treatment such as recrystallization; extraction; distillation; adsorption treatment using activated carbon, silica, alumina and the like; chromatography method such as silica gel column chromatography and the like; etc.

Regarding the steric configurations of a carboxy group and a 2-cyano-1-propenyl group in thus obtainable 3-(2-cyano-1-propenyl)-2,2-dimethylcyclopropanecarboxylic acid or its salt, the steric configurations of a formyl group and a group having an ester bond (COO—) in the ester compound used are usually kept, respectively. That is, when a (1R,3R)-3-(2-cyano-1-propenyl)-2,2-dimethylcyclopropanecarboxylate is used, (1R,3R)-3-(2-cyano-1-propenyl)-2,2-dimethylcyclopropanecarboxylic acid or its salt is usually obtained. Further, 3-(2-cyano-1-propenyl)-2,2-dimethylcyclopropanecarboxylic acid or its salt is usually a mixture of a Z form and an E form. Here, the Z form represents a structure in which a cyano group and a cyclopropane ring are present on mutually the same side of a double bond, and the E form represents a structure in which these are present on mutually the opposite sides of a double bond.

3-(2-cyano-1-propenyl)-2,2-dimethylcyclopropanecarboxylic acid or its salt (hereinafter, generically called carboxylic acid (1) in some cases) can be further subjected to an esterification reaction.

The above-described esterification reaction includes
(a) a method of dehydration-condensing a carboxylic acid (1) and a monohydroxy compound,
(b) a method of converting a carboxylic acid (1) with a halogenating agent into an acid halide, and reacting the resultant acid halide with a monohydroxy compound in the presence of a base catalyst,
(c) a method of converting a carboxylic acid (1) into an esterified compound of a monohydroxy compound having 1 to 4 carbon atoms according to the methods of (a) and (b), and carrying out transesterification of the resultant esterified compound,
and the like.

In the above-described method (a), dehydration-condensation can be carried out by a known method, and a catalyst may be used.

In the above-described method (b), the halogenating agent includes thionyl chloride, phosphorus pentachloride and the like. The base catalyst includes pyridine and the like.

In the above-described method (c), transesterification can be carried out by a known method. Such a method includes, for example, a method of reacting an ester compound and a monohydroxy compound having a desired hydrocarbon group in the presence of a lithium compound, such as lithium methoxide and the like.

The esterification method is preferably the method (a). The above-described method (a) is carried out preferably in the presence of a catalyst, more preferably in the presence of a zirconium compound.

In the above-described esterification methods, the monohydroxy compound includes compounds represented by formula (2):

$$R^2\text{—OH} \quad (2)$$

wherein, $R^2$ represents a chain hydrocarbon group having 1 to 10 carbon atoms or cyclic hydrocarbon group having 3 to 10 carbon atoms which may have at least one substituent selected from the above-described Group A.

and the like.

Specific examples of $R^2$ include the same examples as for the above-described R.

When $R^2$ is a chain hydrocarbon group having 1 to 10 carbon atoms optionally having a substituent, examples of the monohydroxy compound include alkyl alcohols having 1 to 10 carbon atoms, such as a methyl alcohol, ethyl alcohol, n-propyl alcohol, isopropyl alcohol, n-butyl alcohol, sec-butyl alcohol, tert-butyl alcohol, n-pentyl alcohol, neopentyl alcohol, amyl alcohol, n-hexyl alcohol, n-octyl alcohol, n-decyl alcohol and the like; alkyl alcohols having 1 to 10 carbon atoms substituted by a heterocyclic ring, such as a 2-furylmethyl alcohol, 3-furylmethyl alcohol, (5-phenoxy-3-furyl)methyl alcohol, (5-benzyl-3-furyl)methan-1-ol, {5-(difluoromethyl)-3-furyl}methan-1-ol, 5-propargylfurfuryl alcohol, (5-methylisoxazol-3-yl)methan-1-ol, 1-{2-(trifluoromethyl)-1,3-thiazol-4-yl}prop-2-yn-1-ol, 1-{2-(trifluoromethoxy)-1,3-thiazol-4-yl}prop-2-yn-1-ol, 1-{1-prop-2-ynyl-5-(trifluoromethyl)pyrrol-3-yl}prop-2-yn-1-ol, (1-prop-2-ynylpyrrol-3-yl)methan-1-ol, 3-(hydroxymethyl)-1-propynyl-imidazolidine-2,4-dione, 4-hydroxy-3-methyl-2-(2-propenyl)-2-cyclopenten-1-one, 4-hydroxy-3-methyl-2-(2-propynyl)-2-cyclopenten-1-one, 2-(hydroxymethyl)-4,5,6,7-tetrahydroisoindole-1,3-dione, {1-(2-propynyl)pyrrol-3-yl}methan-1-ol, 5-(hydroxymethyl)-4-methyl-(2-propynyl)-1,3-thiazolin-2-one, 4-methylhept-4-en-1-yn-3-ol and the like; haloalkyl alcohols having 1 to 10 carbon atoms, such as chloromethyl alcohol, dichloromethyl alcohol, trichloromethyl alcohol, bromomethyl alcohol, dibromomethyl alcohol, tribromomethyl alcohol, fluoromethyl alcohol, difluoromethyl alcohol, trifluoromethyl alcohol, fluoroethyl alcohol, difluoroethyl alcohol, trifluoroethyl alcohol, tetrafluoroethyl alcohol, pentafluoroethyl alcohol, 3,3-dibromo-2-propen-1-ol, perfluoropropyl alcohol, hexafluoroisopropyl alcohol, perfluorobutyl alcohol, perfluoropentyl alcohol, perfluorohexyl alcohol, perfluorooctyl alcohol, perfluorodecyl alcohol and the like; haloalkyl alcohols having 1 to 10 carbon atoms substituted by a heterocyclic ring, such as {1-(2-propynyl)-5-(trifluoromethyl)-4-pyrazolyl}methan-1-ol, 1-{1-(2-propynyl)-5-(trifluoromethyl)pyrrol-3-yl}prop-2-yn-1-ol, 1-{2-(trifluoromethyl)-1,3-thiazol-4-yl}prop-2-yn-1-ol, 1-{2-(trifluoromethoxy)-1,3-thiazol-4-yl}prop-2-yn-1-ol, 4-fluorohept-4-en-1-yn-3-ol and the like.

When $R^2$ is a cyclic hydrocarbon group having 3 to 10 carbon atoms optionally having a substituent, examples of the monohydroxy compound include optionally substituted benzyl alcohols, such as benzyl alcohol, 2-methyl-3-phenylbenzyl alcohol, 2,3,5,6-tetrafluorobenzyl alcohol, 2,3,5,6-tetrafluoro-4-methylbenzyl alcohol, 2,3,5,6-tetrafluoro-4-methoxybenzyl alcohol, 2,3,5,6-tetrafluoro-4-(methoxymethyl)benzyl alcohol, 2,3,5,6-tetrafluoro-4-allylbenzyl alcohol, 2,3,5,6-tetrafluoro-4-propargylbenzyl alcohol, 2,3,5,6-tetrafluoro-4-(methylthiomethyl)benzyl alcohol, 2,3,5,6-tetrafluoro-4-(difluoromethyl)benzyl alcohol, 2,3,5,6-tetrafluoro-4-(difluoromethoxy)benzyl alcohol, 2,3,5,6-tetrafluoro-4-(2,2,2-trifluoroacetyloxy)methylbenzyl alcohol, 4-(trifluoromethyl)benzyl alcohol, 2,3,4,5-tetrafluoro-6-methylbenzyl alcohol, 3-phenylbenzyl alcohol, 2,6-dichlorobenzyl alcohol, 3-phenoxybenzyl alcohol, (2-methylphenyl)methyl alcohol, (3-methylphenyl)methyl alcohol, (4-methylphenyl)methyl alcohol, (2,3-dimethylphenyl)methyl alcohol, (2,4-dimethylphenyl)methyl alcohol, (2,5-dimethylphenyl)methyl alcohol, (2,6-dimethylphenyl)methyl alcohol, (3,4-dimethylphenyl)methyl alcohol, (2,3,4-trimethylphenyl)methyl alcohol, (2,3,5-trimethylphenyl)methyl alcohol, (2,3,6-trimethylphenyl)methyl alcohol, (3,4,5-trimethylphenyl)methyl alcohol, (2,4,6-trimethylphenyl)methyl alcohol, (2,3,4,5-tetramethylphenyl)methyl alcohol, (2,3,4,6-tetramethylphenyl)methyl alcohol, (2,3,5,6-tetramethylphenyl)methyl alcohol, (pentamethylphenyl)methyl alcohol, (ethylphenyl)methyl alcohol, (propylphenyl)methyl alcohol, (isopropylphenyl)methyl alcohol, (butylphenyl)methyl alcohol, (sec-butylphenyl)methyl alcohol, (tert-butylphenyl)methyl alcohol, (pentylphenyl)methyl alcohol, (neopentylphenyl)methyl alcohol, (hexylphenyl)methyl alcohol, (octylphenyl)methyl alcohol, (decylphenyl)methyl alcohol, (dodecylphenyl)methyl alcohol, (tetradecylphenyl)methyl alcohol and the like; 2-hydroxy-2-(3-phenoxyphenyl)ethanenitrile, 2-hydroxy-2-{4-(methoxymethyl)phenyl}ethanenitrile, 2-{3-(4-chlorophenoxy)phenyl}-2-hydroxyethanenitrile, 2-(4-amino-2,3,5,6-tetrafluorophenyl)-2-hydroxyethanenitrile, 2-(4-fluoro-3-phenoxyphenyl)-2-hydroxyethanenitrilenaphthylmethyl alcohol, anthracenylmethyl alcohol, 1-phenylethyl alcohol, 1-(1-naphthyl)ethyl alcohol, 1-(2-naphthyl)ethyl alcohol, 4-prop-2-ynylphenyl)methan-1-ol, 3-prop-2-ynylphenyl)methan-1-ol, (1-prop-2-ynyl-2-methylindol-3-yl)methan-1-ol, {1-prop-2-ynyl-2-(trifluoromethyl)indol-3-yl}methan-1-ol, 4-prop-2-enylindan-1-ol, 4-phenylindan-2-ol, 4-(2-thienyl)indan-2-ol, (2,3,6-trifluoro-4-pyridyl)methan-1-ol, and alkoxyaralkyl alcohols obtained by optionally changing a halogen atom in the above-described haloaralkyl alcohols into methoxy, ethoxy, propoxy, isopropoxy, butoxy, sec-butoxy, tert-butoxy and the like, and cyanoaralkyl alcohol, nitroaralkyl alcohol, phenol, 1-naphthol, 2-naphthol, 4-prop-2-ynylphenol, 3-prop-2-ynylphenol, 4-hydroxyacetophenone, 4-hydroxybenzaldehyde, and, those obtained by substituting an aromatic ring of these compounds with an alkyl group, alkoxy group, halogen atom or the like; etc.

Examples of the monohydroxy compound include preferably primary alcohols and benzyl alcohols, more preferably optionally substituted primary alcohols having 1 to 10 carbon atoms and optionally substituted benzyl alcohols, further preferably benzyl alcohols optionally substituted by a halogen, alkoxy group, alkyl group, allyl group or alkenyl group, particularly preferably 2,3,5,6-tetrafluoro-4-(methoxymethyl)benzyl alcohol, 2,3,5,6-tetrafluoro-4-methylbenzyl alcohol, 2,3,5,6-tetrafluoro-4-allylbenzyl alcohol, 2,3,5,6-tetrafluoro-4-propargylbenzyl alcohol, 2,3,5,6-tetrafluoro-4-(methylthiomethyl)benzyl alcohol and the like.

The use amount of the monohydroxy compound is usually 1 mol or more with respect to 1 mol of the carboxylic acid (1), if necessary, it may be used in excess amount, and it may also be used as a solvent. In general, after completion of the esterification reaction, unreacted monohydroxy compounds can also be recovered by an operation such as, for example, distillation, extraction, liquid separation and the like.

The zirconium compound includes, for example, Lewis acidic zirconium compounds and the like, more preferably compounds represented by formula (3):

$$Zr(O)_m(X)_n(Y)_{4-2m-n} \quad (3)$$

(wherein, X and Y represent each independently a halogen atom, alkoxy group having 1 to 10 carbon atoms, acyloxy group having 2 to 10 carbon atoms, acetylacetonate group, amino group, di(C1 to C4 alkyl)amino group or cyclopentadienyl group, m represents 0 or 1, and n represents 0, 1 or 2).

Specific examples of the zirconium compound include zirconium tetrafluoride, zirconium tetrachloride, zirconium tetrabromide, zirconium tetraiodide, zirconium acetate, zirconium acetylacetonate, zirconium ethoxide, zirconium n-propoxide, zirconium i-propoxide, zirconium n-butoxide, zirconium t-butoxide, zirconium oxychloride, tetrakis(dimethylamino)zirconium, tetrais(diethylamino)zirconium, zirconocene dichloride, zirconocene dimethoxide, decamethylzirconocene dichloride and the like, preferably halogen zirconium and zirconium alkoxides having 1 to 5 carbon atoms, more preferably zirconium tetrachloride, zirconium n-propoxide.

As the zirconium compound, commercially available anhydrides or hydrates can be used as they are. Further, complexes with a compound having a coordinating property such as tetrahydrofuran, tetramethylethylenediamine and the like can also be used.

The used amount of the zirconium compound is in the range of usually 0.001 to 200 mol, preferably about 0.01 to about 10 mol with respect to 1 mol of the carboxylic acid (1).

The esterification reaction of the carboxylic acid (1) and the monohydroxy compound (2) in the presence of a zirconium compound is preferably carried out under an atmosphere of an inert gas, such as argon, nitrogen and the like. The esterification can be carried out under any of normal pressure, increased pressure and reduced pressure, preferably under normal pressure or reduced pressure. It is preferable that the reaction is carried out while continuously removing water which is a by-product of the dehydration condensation reaction out of the reaction system by a method such as distillation and the like.

The esterification reaction can be carried out usually at a temperature in the range of about 20 to 200° C.

By the esterification reaction, a reaction mixture containing a 3-(2-cyano-1-propenyl)-2,2-dimethylcyclopropanecarboxylate represented by formula (4):

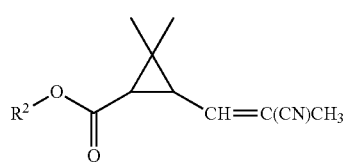

(4)

wherein, $R^2$ represents the same meaning as described above; can be obtained. The reaction mixture can be further washed with water or acidic water, to remove a catalyst, and if necessary, purification operations such as distillation, recrystallization, column chromatography and the like may also be carried out.

Thus obtained 3-(2-cyano-1-propenyl)-2,2-dimethylcyclopropanecarboxylate can be used, for example, in pest control agents described in JP-A No. 2004-2363, and the like.

Specific examples of the 3-(2-cyano-1-propenyl)-2,2-dimethylcyclopropanecarboxylate include 4-methoxymethyl-2,3,5,6-tetrafluorobenzyl 3-(2-cyano-1-propenyl)-2,2-dimethylcyclopropanecarboxylate, 4-methyl-2,3,5,6-tetrafluorobenzyl 3-(2-cyano-1-propenyl)-2,2-dimethylcyclopropanecarboxylate, 4-allyl-2,3,5,6-tetrafluorobenzyl 3-(2-cyano-1-propenyl)-2,2-dimethylcyclopropanecarboxylate, 4-propargyl-2,3,5,6-tetrafluorobenzyl 3-(2-cyano-1-propenyl)-2,2-dimethylcyclopropanecarboxylate, 4-methylthiomethyl-2,3,5,6-tetrafluorobenzyl 3-(2-cyano-1-propenyl)-2,2-dimethylcyclopropanecarboxylate and the like, and those obtained by substituting an ester portion in these compounds by the correspondent monohydroxy compound; etc.

A production method comprising a first step of reacting the above-described 3-formyl-2,2-dimethylcyclopropanecarboxylate and propionitrile in the presence of a base, and a second step, of reacting 3-(2-cyano-1-propenyl)-2,2-dimethylcyclopropanecarboxylic acid or its salt obtained in the above-described first step and a monohydroxy compound represented by formula (2):

$$R^2-OH \qquad (2)$$

(wherein, $R^2$ represents the same meaning as described above), in the presence of a zirconium compound, to obtain a 3-(2-cyano-1-propenyl)-2,2-dimethylcyclopropanecarboxylate represented by formula (4):

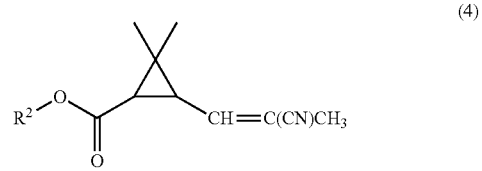

(4)

(wherein, $R^2$ represents the same meaning as described above)
is also an aspect of the present invention.

EXAMPLES

The present invention will be illustrated more in detail by examples below, but the present invention is not limited to these examples.

In the examples, gas chromatography was carried out according to an internal standard method using GC-17A manufactured by SHIMADZU Corp.

In the examples, the Z form ratio means the production ratio represented by Z form/(Z form+E form).

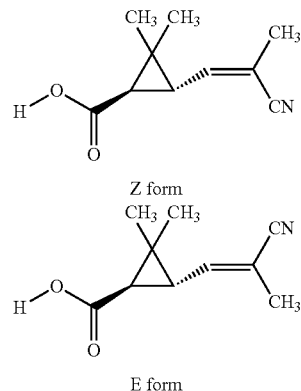

Example 1

Sixteen point two grams (16.2 g) of methyl (1R,3R)-3-formyl-2,2-dimethylcyclopropanecarboxylate, 6.9 g of propionitrile and 80.8 g of dimethyl sulfoxide were mixed at room temperature, to this was added 11.7 g of potassium hydroxide and the mixture was stirred for 1.5 hours. The resultant mixture was heated up to 45° C., and the mixture was further stirred for 1 hour. The reaction mixture was cooled down to room temperature, to this was added 154.9 g of a 1 wt % sodium hydroxide solution, further, 48.5 g of xylene was added and the mixture was stirred, then, the liquid was separated. To the resultant aqueous layer was added 80.8 g of xylene, 34 g of a 70 wt % sulfuric acid solution was dropped into the resultant mixture while cooled with ice, then, the liquid was separated to obtain an oil layer. To the resultant aqueous layer was added 48.5 g of xylene and extraction thereof was performed at room temperature, and the resultant oil layer and the oil layer obtained previously were combined, and washed with 48.5 g of water. The resultant oil layer was concentrated under reduced pressure to obtain 13.4 g of an oil consisting chiefly of (1R,3R)-3-(2-cyano-1-propenyl)-2,2-dimethylcyclopropanecarboxylic acid. This was analyzed by gas chromatography (internal standard method) to find that the yield was 69% and the Z form ratio was 67%.

Example 2

One point zero gram (1.0 g) of methyl (1R,3R)-3-formyl-2,2-dimethylcyclopropanecarboxylate, 0.41 g of propionitrile and 10 g of dimethyl sulfoxide were mixed at room temperature, to this was added 0.82 g of potassium hydroxide and the mixture was stirred at room temperature for 2 hours. The resultant reaction mixture was analyzed by gas chromatography (internal standard method) to find that the yield of (1R,3R)-3-(2-cyano-1-propenyl)-2,2-dimethylcyclopropanecarboxylic acid was 78% and the Z form ratio thereof was 67%.

Example 3

The same reaction as in Example 2 was carried out excepting that 2.08 g of cesium hydroxide monohydrate was used instead of 0.82 g of potassium hydroxide and the mixture was stirred at 45° C. for 1 hour in Example 2. The yield of (1R, 3R)-3-(2-cyano-1-propenyl)-2,2-dimethylcyclopropanecarboxylic acid was 84% and the Z form ratio thereof was 64%.

Example 4

A mixture of 0.70 g of propionitrile, 5.0 g of dimethyl sulfoxide and 0.73 g of potassium hydroxide was adjusted to 45° C., and into this mixture, a mixed solution of 1.0 g of methyl (1R,3R)-3-formyl-2,2-dimethylcyclopropanecarboxylate and 5.0 g of dimethyl sulfoxide was dropped over a period of 1 hour. The internal temperature of the mixture during dropping was in the range of 45 to 47° C. The resultant mixture was stirred at 48° C. for 3 hours. The resultant reaction mixture was cooled down to room temperature, and analyzed by gas chromatography (internal standard method) to find that the yield of (1R,3R)-3-(2-cyano-1-propenyl)-2,2-dimethylcyclopropanecarboxylic acid was 83% and the Z form ratio thereof was 61%.

Example 5

To a mixed solution of 1.0 g of methyl (1R,3R)-3-formyl-2,2-dimethylcyclopropanecarboxylate and 10.0 g of propionitrile was added 1.44 g of potassium tert-butoxide at room temperature, the resultant mixture was heated up to 45° C. and stirred at the same temperature for 1 hour. The resultant reaction mixture was cooled down to room temperature and analyzed by gas chromatography (internal standard method) to find that the yield of (1R,3R)-3-(2-cyano-1-propenyl)-2,2-dimethylcyclopropanecarboxylic acid was 54% and the Z form ratio thereof was 63%.

Example 6

A mixture of 2.24 g of 2,3,5,6-tetrafluoro-4-methoxymethyl-benzyl alcohol, 70 mg of zirconium chloride and 20 ml of xylene was refluxed by heating at 145° C. for about 10 minutes, then, 10 ml of xylene was distilled off. The resultant mixture was allowed to cool to 80° C., to this was added 1.97 g of (1R,3R)-3-(2-cyano-1-propenyl)-2,2-dimethylcyclopropanecarboxylic acid obtained in Example 1, and the resultant mixture was stirred at the xylene reflux temperature while removing water by-produced out of the reaction system under the xylene azeotropic condition, to obtain 2,3,5,6-tetrafluoro-4-methoxymethyl-benzyl (1R,3R)-3-(2-cyano-1-propenyl)-2,2-dimethylcyclopropanecarboxylate.

Example 7

A mixture of 8.0 g of 2,3,5,6-tetrafluoro-4-methoxymethyl-benzyl alcohol, 0.3 g of a 70 wt % zirconium tetraisopropoxide/2-propanol solution and 55 g of xylene was refluxed by heating at 145° C., then, 39 g of the distilled oil was removed. The resultant mixture was allowed to cool to 80° C., to this was added 7.4 g of (1R,3R)-3-(2-cyano-1-propenyl)-2,2-dimethylcyclopropanecarboxylic acid obtained in Example 1, and the resultant mixture was stirred at the xylene reflux temperature while removing water by-produced out of the reaction system under the xylene azeotropic condition to obtain 2,3,5,6-tetrafluoro-4-methoxymethyl-benzyl (1R,3R)-3-(2-cyano-1-propenyl)-2,2-dimethylcyclopropanecarboxylate.

INDUSTRIAL APPLICABILITY

The present invention is capable of producing 3-(2-cyano-1-propenyl)-2,2-dimethylcyclopropanecarboxylic acid or its salt which is a compound useful as a pest control agent and its intermediate.

The invention claimed is:

1. A process for producing 3-(2-cyano-1-propenyl)-2,2-dimethylcyclopropanecarboxylic acid or its salt comprising reacting a 3-formyl-2,2-dimethylcyclopropanecarboxylate and propionitrile in the presence of a base.

2. The process according to claim 1, wherein the base is a strong base.

3. The process according to claim 1, wherein the base is at least one base selected from the group consisting of alkali metal hydroxides, alkaline earth metal hydroxides, transition metal hydroxides, tetraalkylammonium hydroxides, alkali metal alkoxides and phosphazene compounds.

4. The process according to claim 1, wherein the base is at least one base selected from the group consisting of alkali metal hydroxides, alkaline earth metal hydroxides, transition metal hydroxides and tetraalkylammonium hydroxides.

5. The process according to claim 1, wherein the base is an alkali metal hydroxide or alkaline earth metal hydroxide.

6. The process according to claim 1, wherein the base is potassium hydroxide or cesium hydroxide.

7. The process according to claim 1, wherein a 3-formyl-2,2-dimethylcyclopropanecarboxylate and propionitrile are reacted in the presence of a solvent.

8. The process according to claim 7, wherein the solvent is an ether solvent or sulfoxide solvent.

9. The process according to claim 7, wherein the solvent is tetrahydrofuran or dimethyl sulfoxide.

10. A process for producing a 3-(2-cyano-1-propenyl)-2,2-dimethylcyclopropanecarboxylate represented by formula (4):

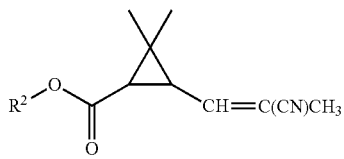 (4)

wherein, $R^2$ represents a chain hydrocarbon group having 1 to 10 carbon atoms or cyclic hydrocarbon group having 3 to 10 carbon atoms each of which optionally have at least one substituent selected from the following Group A;

Group A: halogen atoms, acyl groups having 2 to 7 carbon atoms, alkoxy groups having 1 to 7 carbon atoms optionally having a substituent, alkylthio groups having 1 to 3 carbon atoms and aryl groups having 6 to 10 carbon atoms optionally having a substituent;

comprising a first step of reacting a 3-formyl-2,2-dimethylcyclopropanecarboxylate and propionitrile in the presence of a base, and a second step of reacting 3-(2-cyano-1-propenyl)-2,2-dimethylcyclopropanecarboxylic acid or its salt obtained in said first step and a monohydroxy compound represented by formula (2):

$R^2$—OH (2)

wherein, $R^2$ represents the same meaning as described above; in the presence of a zirconium compound.

* * * * *